United States Patent [19]

North et al.

[11] Patent Number: 5,686,598
[45] Date of Patent: Nov. 11, 1997

[54] GENES ASSOCIATED WITH RETINAL DYSTROPHIES

[75] Inventors: Michael North, San Diego, Calif.; Patsy Nishina; Juergen Naggert, both of Bar Harbor, Me.

[73] Assignees: The Jackson Laboratory, Bar Harbor, Me.; Sequana Therapeutics, Inc., La Jolla, Calif.

[21] Appl. No.: 701,380

[22] Filed: Aug. 22, 1996

[51] Int. Cl.[6] ................................................ C07H 21/04
[52] U.S. Cl. ............................................................ 536/23.5
[58] Field of Search ............................................. 536/23.5

[56] References Cited

PUBLICATIONS

North, MA et al. Proc Nat Acad Sci (USA). 94: 3128–3133 Apr. 1, 1997.

*Primary Examiner*—Christina Y. Chan
*Assistant Examiner*—F. Pierre VanderVegt
*Attorney, Agent, or Firm*—Fish & Richardson P.C.; Pamela J. Sherwood

[57] ABSTRACT

The gene responsible for the autosomal recessive retinal degenerative disease RP 14 is identified, TULP1. The genes are used to produce the encoded protein; in screening for compositions that modulate the expression or function of TULP1 protein; and in studying associated physiological pathways. The DNA is further used as a diagnostic for genetic predisposition to retinal degeneration.

2 Claims, No Drawings

GENES ASSOCIATED WITH RETINAL DYSTROPHIES

INTRODUCTION

1. Technical Field

The field of this invention is genes associated with retinal dystrophies.

2. Background

Vision is fundamentally important throughout life. However, the eye can be a fragile organ, and is susceptible to a number of hereditary and/or age related degenerative disorders. In the United States, a common cause of irreversible blindness or severe loss of vision is retinal dystrophies. The retina is the sensory tunic of the eye, containing light sensitive receptors, a complex of neurons, and pigmented epithelium, arranged in discrete layers. In humans, the macula is the portion of the retina that lies directly behind the lens. Cones, the photoreceptor cells responsible for central vision, are heavily concentrated in the macula. Central dystrophies, which affect the macula, include Best's disease, age-related macular degeneration, and Stargardt's macular dystrophy. The peripheral retina is composed mainly of rods, which are responsible for side and night vision. Peripheral degenerative retinal diseases include retinitis pigmentosa, choroidemia and Bietti's crystalline dystrophy.

Macular degenerations are a heterogenous group of diseases, characterized by progressive central vision loss and degeneration of the macula and underlying retinal pigmented epithelium. Age-related macular degeneration (ARMD) is the most common form of the disease, affecting an estimated 20% of persons over 75 years of age. However, ARMD is poorly understood in terms of etiology and pathogenesis. The very late onset of the disease has made genetic mapping particularly difficult. Certain macular degenerative conditions with a clear genetic basis, such as Stargardt's and Best's diseases, share many features with ARMD, but have been more amenable to molecular and genetic analysis.

Hereditary peripheral retinopathies are also relatively common. Retinitis pigmentosa (RP), for example, affects approximately 1.5 million people worldwide. Substantial genetic heterogeneity has been observed in this condition, with over 20 chromosomal loci identified. A predisposition to retinitis pigmentosa can be inherited by autosomal dominant, autosomal recessive, X-linked or digenic mode. Mutations have been identified in seven genes, four of which encode proteins in the rod phototransduction cascade: rhodopsin, alpha and beta subunits of rod cGMP phosphodiesterase, and rod cGMP cation-gated channel protein α subunit. Mutations in the peripherin/RDS gene have been linked to both retinitis pigmentosa and macular degeneration. A single peripherin/RDS mutation apparently caused retinitis pigmentosa, pattern dystrophy and fundus flavimaculitis, in different family members.

In spite of causal heterogeneity, there is significant clinical similarity among RP subtypes. Common signs and symptoms include early electroretinographic abnormalities, ophthalmoscopic findings, and protracted, contiguous expansion of the ring-like scotoma toward the macula, leading to progressively worsening tunnel vision. A recent hypothesis is that active photoreceptor cell death, which is characteristic of these genetically distinct disorders, is mediated by a common induction of apoptosis. If true, it may be possible to treat these conditions by the administration of agents that block induction of apoptosis in photoreceptors, such as neurotrophic factors.

It has been previously shown that the mouse mutation, tubby, leads to early progressive retinal and cochlear degeneration, as well as late-onset obesity, insulin resistance and impaired glucose tolerance. Identification by positional cloning revealed a novel gene, which is a member of a gene family with a highly conserved carboxyterminus and variable amino terminus. The prevalence and clinical consequences of retinal dystrophies make it of interest to determine whether other members of this gene family may be associated with retinal disease.

Relevant Literature

Shugart et al. (1995) *Am J Hum Genet*, 57:499–502 disclose fine genetic mapping of a gene for autosomal recessive retinitis pigmentosa on chromosome 6p21. Berson (1996) *Proc Natl Acad Sci USA* 93:4526–4528 review retinitis pigmentosa. Overviews of photoreceptor dystrophies may be found in Cotlier et al. (1995) *Surv. Ophthalmology* 40:51–61; Bird (1995) *Am. J. Ophthal.* 119: 543–562; and Adler (1996) *Arch Ophthal,* 114:79–83.

Bennett et al. (1996) *Nature Medicine* 2:649 demonstrate that injection into rd/rd mice of a recombinant replication defective adenovirus that contains wild-type cDNA encoding βPDE delays photoreceptor death. Adenovirus vectors are described in Englehardt et al. (1993) *Nature Genetics* 4:27–34, and in Wang and Finer (1996) *Nature Medicine* 2:714.

The mouse tub mutation is described in Coleman and Eicher (1990) *J Hered* 81:424–7 as an autosomal recessive mutation located on chromosome 7, which causes slowly developing but ultimately severe obesity. Ohlemiller et al. (1995) *Neuroreport* 6:845–9 and Heckenlively et al. (1995) *P.N.A.S.* 92:11100–11104 describe hearing loss and progressive retinal degeneration in tubby mice. The retinal degeneration is characterized by loss of photoreceptor cells, resulting in abnormal electroencephalograms by 3 weeks of age. Noben-Trauth et al. (1996) *Nature* 380:534–538 and Kleyn et al. (1996) *Cell* 65:281–290 describe the human and mouse genes associated with tubby.

SUMMARY OF THE INVENTION

Nucleic acid compositions are provided that encode a mammalian retina-specific protein, TULP1. The human TULP1 locus is associated with a genetic predisposition to peripheral retinal degeneration. The nucleic acid compositions find use in identifying DNA sequences encoding homologous or related proteins; for production of the encoded protein; and in studying associated physiological pathways. In addition, modulation of the gene activity in vivo is used for prophylactic and therapeutic purposes, such as treatment of retinal degeneration, identification of retinal cells based on expression, and the like. The DNA is further used as a diagnostic for genetic predisposition to retinal degeneration.

BRIEF DESCRIPTION OF THE SEQUENCES

The complete cDNA sequence of human TULP1 is provided in SEQ ID NO:1, (the coding region starts at position 37) and its predicted amino acid sequence in SEQ ID NO:2.

DESCRIPTION OF THE SPECIFIC EMBODIMENTS

Mammalian genes associated with retinal degeneration are provided (TULP1). Of particular interest are the human gene sequences. The TULP1 locus is associated with a predisposition to retinitis pigmentosa. TULP1 nucleic acid compositions are used to identify homologous or related genes, to identify retinal cells based on gene expression, to produce the corresponding protein, and as a diagnostic for a specific genetic predisposition to late onset blindness. The encoded protein is useful as an immunogen to raise antibodies that specifically identify retinal cells, in drug screening assays directed at retinal degeneration, and for therapeutic purposes.

The tubby gene family is a group of related genes characterized by a highly conserved carboxy terminus and variable amino terminus. While tubby is expressed in a number of different cell types, the expression of TULP1 is restricted to the retina. It will be understood by one of skill in the art that low basal levels of transcription may be present in other normal cell types, or that a relatively rare cell type may have a high level of expression that cannot readily be detected in mRNA prepared from whole tissue. By specific expression, it is intended that mRNA levels are increased above the basal levels observed in non-retinal cells by at least about 100 fold, more usually by at least about 1000 fold. It will be further understood that malignant, or transformed, cells may express genes in an aberrant fashion.

The DNA sequence encoding TULP1 may be cDNA or genomic DNA or a fragment thereof. The term "gene" shall be intended to mean an open reading frame encoding a specific TULP1 polypeptide, as well as adjacent 5' and 3' non-coding nucleotide sequences involved in the regulation of expression, up to about 1 kb beyond the coding region, in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons, 3' and 5' non-coding regions. Normally mRNA species have contiguous exons, with the intervening introns deleted, to create a continuous open reading frame.

Genomic TULP1 sequences have non-contiguous open reading frames, where introns interrupt the coding regions. A genomic sequence of interest comprises the nucleic acid present between an initiation codon and stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb of flanking genomic DNA at either the 5' or 3' end of the coding region. The genomic DNA may be isolated as a fragment of 50 kbp or smaller. A preferred genomic sequence will lack those sequences that are linked to TULP1 in a native chromosome but which do not contribute to the biological function of the TULP1 gene.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA sequences are obtained in substantial purity, generally as a sequence other than a sequence of an intact mammalian chromosome. Usually, the DNA will be obtained substantially free of other nucleic acid sequences that do not include a TULP1 sequence or fragment thereof, generally being at least about 50%, usually at least about 90% pure and are typically "recombinant", i.e. flanked by one or more nucleotides with which it is not normally associated on a naturally occurring chromosome.

The DNA sequences may be used in a variety of ways. They may be used as probes for identifying other TLP polypeptides, including novel subfamily members, homologs and syntenic homologs. Mammalian homologs have substantial sequence similarity to the subject sequences, i.e. at least 80%, preferably at least 90%, more preferably at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithims for sequence analysis are known in the art, such as BLAST, described in Altschul et al. (1990) *J Mol Biol* 215:403–10.

Nucleic acids having sequence similarity are detected by hybridization under low stringency conditions, for example, at 50° C. and 10×SSC (0.9M saline/0.09M sodium citrate) and remain bound when subjected to washing at 55° C. in 1×SSC. By using probes, particularly labeled probes of DNA sequences, one can isolate homologous or related genes. The source of homologous genes may be any mammalian species, e.g. primate species, particularly human; murines, such as rats and mice, canines, felines, bovines, ovines, equines, etc.

For hybridization probes, it may be desirable to use nucleic acid analogs, in order to improve the stability and and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The DNA sequences, particularly nucleic acid analogs as described above, may be used as antisense sequences. The antisense sequences may be used by themselves or in conjunction with various toxic moieties, such as metal chelates, sensitizers, ribozymes, and the like. Antisense sequences may be used to study the effect of TULP1 loss of function.

The DNA may also be used to identify expression of the gene in a biological specimen, e.g. retinal cells. The manner in which one probes cells for the presence of particular nucleotide sequences, as genomic DNA or RNA, is well-established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is fractionated by gel electrophoresis, transferred to a suitable support, e.g. nitrocellulose and then probed with a fragment of the subject DNA as a probe. Other techniques may also find use. Detection of mRNA having the subject sequence is indicative of TULP1 gene expression in the sample.

The TULP1 genes and fragments thereof, encoded protein, and anti-TULP1 antibodies are useful in the identification of individuals predisposed to retinal dystrophies. Of particular interest are peripheral retinal dystrophies, such as retinitis pigmentosa. The characterization is useful in determining further treatment of the patient. DNA from a patient having a retinal dystrophy, e.g. retinitis pigmentosa, that may be associated with a TULP1 gene is analyzed for the presence of a predisposing, degenerative mutation in the gene. The presence of a mutated TULP1 sequence that affects the activity or expression of the encoded gene product confers an increased susceptibility to this condition. Specific mutations of interest include any mutation that leads to retinal degeneration, including insertions, substitutions and deletions in the coding region sequence, introns that affect splicing, promoter or enhancer that affect the activity and expression of the protein. A "normal" cDNA sequence of human TULP1 is provided in SEQ ID NO:1. The normal TULP1 sequence shall be understood to include sequence variants in non-coding regions that do not affect the level of expression of the gene, coding region variants that do not change the amino acid sequence, e.g. "third position" changes, and changes that result in an altered amino acid sequence but maintain substantially all of the normal protein function.

Biochemical studies may be performed to determine whether a candidate mutation in the TULP1 coding region or control regions predisposes to disease. For example, the activity of a candidate TULP1 protein may be compared with the wild-type protein activity. A change in the promoter or enhancer sequence that downregulates expression of TULP1 may also result in predisposition to retinal degeneration. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, chloramphenicol acetyltransferase, etc. that provides for convenient quantitation; and the like.

Retinal dystrophies of interest also include Stargardt's macular dystrophy, Best's disease, pigment pattern dystrophies, central alveolar choroidal dystrophy, dominant drusen, hereditary hemorrhagic macular dystrophy, North Carolina macular dystrophy, pericentral choroidal dystrophy, adult foveomacular dystrophy, benign concentric annular macular dystrophy, central aureolar pigment epithelial dystrophy, congenital macular coloboma, dominantly inherited cystoid macular edema, familial foveal retinoschisis, fenestrated sheen macular dystrophy, progressive foveal dystrophy, slowly progressive macular dystrophy, Sorsby's pseudoinflammatory dystrophy, cone-rod dystrophy, progressive cone dystrophy, Leber's congenital amaurosis, Goldman-Favre syndrome.

A number of methods are used to determine the presence of a predisposing mutation in an individual. Genomic DNA is isolated from the individual or individuals that are to be tested, from any nucleated cellular source, such as blood, hair shafts, saliva, mucous, biopsy, feces, etc. Where large amounts of DNA are available, the genomic DNA may be used directly. Alternatively, the region of interest is cloned into a suitable vector and grown in sufficient quantity for analysis, or amplified by conventional techniques.

Methods using PCR amplification can be performed on the DNA from a single cell, although it is convenient to use at least about $10^5$ cells. A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high afifnity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to the normal TULP1 sequence. Alternatively, where the predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilised on a solid support, as described in WO 95/11995, may also be used as a means of detecting the presence of variant sequences.

The subject nucleic acids can be used to generate transgenic animals or site specific gene modifications in cell lines. The modified cells or animals are useful in the study of TULP1 function and regulation. For example, a series of small deletions or substitutions may be made in the TULP1 gene to determine the role of different coding regions in retinal degeneration, signal transduction, substrate binding, etc.

DNA constructs for homologous recombination will comprise at least a portion of the TULP1 gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the modified TULP1 gene and males and females having the modification are mated to produce homozygous progeny. The transgenic animals may be any non-human mammal, such as laboratory animals, domestic animals, etc. The transgenic animals may be used to determine the effect of a candidate drug on retinal degeneration in an in vivo environment.

Investigation of gene function may also utilize non-mammalian models, particularly using those organisms that are biologically and genetically well-characterized, such as *C. elegans, D. melanogaster* and *S. cerevisiae*. The subject gene sequences may be used to complement defined genetic lesions in order to determine the physiological and biochemical pathways involved in TULP1 function. A number of human genes have been shown to complement mutations in lower eukaryotes. Drug screening may be performed in combination with complementation studies. Many mammalian genes have homologs in yeast and lower animals. The study of such homologs' physiological role and interactions with other proteins can facilitate understanding of biological function. In addition to model systems based on genetic complementation, yeast has been shown to be a powerful tool for studying protein-protein interactions through the two hybrid system described in Chien et al. (1991) *P.N.A.S.* 88:9578–9582.

To produce TULP1 proteins the DNA sequences are expressed by insertion into an appropriate expression vector, where the native transcriptional initiation region may be employed or an exogenous transcriptional initiation region, i.e. a promoter other than the promoter which is associated with the gene in the normally occurring chromosome. The promoter is operably linked to the coding sequence of a TULP1 gene to produce a translatable mRNA transcript. The promoter may be introduced by recombinant methods in vitro, or as the result of homologous integration of the sequence into a chromosome. A wide variety of constitutive or inducible promoters are known for a wide variety of expression hosts, where the expression hosts may be prokaryotes or eukaryotes, particularly *E. coli; B. subtilis*; yeast cells; mammalian cells; e.g. Cos cells, HeLa cells, L(tk-), primary cultures; insect cells; *Xenopus laevis* oocytes; and the like. Many strong promoters for mammalian cells are known in the art, including the β-actin promoter, SV40 early and late promoters, immunoglobulin promoter, human cytomegalovirus promoter, retroviral LTRs, etc.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the TULP1 gene or fragment thereof, and a transcriptional termination region. Of particular interest is the use of sequences that allow for the expression of functional epitopes or domains, usually at least about 24 nucleotides in length, more usually at least about 48 nucleotides in length, and up to the complete open reading frame of the gene. After introduction of the DNA, the cells containing the construct may be selected by means of a selectable marker, the cells expanded and then used for expression.

The expression cassettes may be introduced into a variety of vectors, e.g. plasmid, BAC, YAC, bacteriophage such as lambda, P1, M13, etc., animal or plant viruses, and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high-copy copy number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, e.g. conjugation, bacterial transformation, calcium-precipitated DNA, electropotation, fusion, transfection, infection with viral vectors, biolistics, etc.

The DNA sequence may encode amino acid sequences that differ from the native sequence of a TULP1 polypeptide. The sequence may encode polypeptide analogs, fragments or derivatives of substantially similar polypeptides that differ from the naturally-occurring forms in terms of the identity of location of one or more amino acid residues (deletion analogs containing less than all of the residues specified for the protein, substitution analogs wherein one or more residues are replaced by other residues and addition analogs wherein one or more amino acid residues are added to a terminal or medial portion of the polypeptides) and which share some or all of the properties of naturally-occurring forms. Of particular interest are mutations that confer a genetic predisposition to retinal degeneration.

Sequence analogs include the incorporation of preferred codons for expression in non-mammalian host cells; the provision of sites for cleavage by restriction endonuclease enzymes; the addition of promoters operatively linked to enhance RNA transcription; and the provision of additional initial, terminal or intermediate DNA sequences that facilitate vector construction.

With the availability of the protein in large amounts by employing an expression host, the protein may be isolated and purified in accordance with conventional ways. A lysate may be prepared from the expression host and purified using HPLC, exclusion chromatography, gel electrophoresis, affinity chromatography, or other purification techniques as known in the art. The purified protein will generally be at least about 80% pure, preferably at least about 90% pure, and may be up to 100% pure. By pure is intended free of other proteins, as well as cellular debris.

Polypeptides may be used for the production of antibodies. Antibodies are prepared in accordance with conventional methods, where the expressed polypeptide or protein is used as an immunogen, by itself or conjugated to known immunogenic carriers, e.g. KLH, BSA, etc. Various adjuvants may be employed, as appropriate. For monoclonal antibodies, after one or more booster injections, the spleen of the immunized animal is isolated, the splenocytes immortalized, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. The antibodies find use in diagnostic assays for detection of the presence of TULP1 in patient samples, and as a means of identifying retinal cells.

By providing for the production of large amounts of TULP1 protein, one can identify ligands or substrates that bind to, or modulate the action of TULP-1. The purified protein may be used for determination of three-dimensional crystal structure, which can be used for modeling intermolecular interactions. The subject polypeptides or functional domains thereof are used to screen for agonists or antagonists that modulate the interaction of TULP1 with its normal substrate, or proteins with which TULP1 interacts in a normal cell. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like.

The term "agent" as used herein describes any molecule, protein, or pharmaceutical with the capability of mimicking, or directly or indirectly altering the physiological function of TULP1. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used.

The mixture of components are added in any order that provides for the requisite binding. Incubations are performed at any temperature that facilitates optimal activity, typically between 4° and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of retinal degeneration attributable to a defect in TULP1 function. The inhibitory agents may be administered in a variety of ways, orally, parenterally e.g. subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as ocular implants, granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value.

The present data suggest that TLP proteins are associated with degeneration of specific neural cells, e.g. photoreceptors, in the retina. The disease histology is consistent with apoptosis of affected cells. The availability of the subject gene sequences provides a means of analyzing the biology and biochemistry of specific retinal degeneration through in vitro and in vivo drug screening, the use of transgenic animals, complementation of specific genetic lesions, etc., as previously described.

A pathways of particular interest is photoreceptor apoptosis. Mutations in the β subunit of cGMP phosphodiesterase cause retinal degeneration in mice with the rd1 mutation and in humans, and in rd1/rd1 mice an abnormal accumulation of cGMP appears to trigger apoptosis of the photoreceptor cells.

Drug screening assays may be performed with mutant and wild-type TULP1 protein to detect agents that mimic, act as agonists or antagonists for TULP1 function. The interaction of TLP with other proteins in these pathways is of particular interest, and may be detected in a variety of assays, e.g. yeast two hybrid system, in vitro protein-protein binding assays, genetic complementation, etc. There are a number of characterized genes and gene products that operate to regulate or effect apoptosis.

Complementation in animal and yeast models is particularly useful in the study of apoptosis. The genetics of programmed cell death has been well-defined in several animal models. Both C. elegans and D. melanogaster regulate apoptosis through the expression of two gene products, ced-3 and ced-9, and rpr and hid, respectively. The relative simplicity of these pathways is attractive for biochemical and genetic analysis. Both animals are used as screening tools in conjunction with the subject gene sequences, and with their corresponding TULP1 homologs.

A number of apoptotic and anti-apoptotic genes are expressed in neurons and photoreceptors, and may be involved in retinal degeneration. These cells depend on factors such as nerve growth factor and brain derived neurotrophic factor for survival, and may undergo apoptosis where the factor or its receptor are mutated. Among the anti-apoptotic genes of interest are bcl-2, bcl-xL and mcl-1. Inducers of apoptosis include fas (CD95), myc, bax, bcl-xs, TNF receptor and the family of cysteine proteases that includes interleukin 1 β-converting enzyme.

The subject TULP1 genes are useful in gene therapy to prevent the photoreceptor death caused by TULP1 associated retinitis pigmentosa (RP-14). The autosomal recessive nature of RP-14 indicates that delivery of an functional gene to the appropriate retinal photoreceptors will prevent onset of the disease. Of particular interest is intraocular gene delivery, e.g. sub-retinal injection, ocular implants, etc. The therapeutic gene is delivered through a suitable vector, e.g. a plasmid or viral vector. Viral vectors known in the art include modified retroviral genomes such as moloney leukemia virus and human immunodeficiency virus. Retroviral vectors typically include viral sequences that are required for packaging, integration and expression of the inserted TULP1 genes. The vectors are "defective" in the ability to encode viral proteins required for productive infection. Replication requires growth in a packaging cell line that provides the gag, pol, and env proteins necessary for completion of the infectious cycle. Adenovirus vectors are also of interest, as described in Li et al. (1994) Invest. Ophthalmol. Vis. Sci, 35:2543–2549; and Bennett et al. supra.

The following examples are offered by way of illustration and not by way of limitation.

EXPERIMENTAL

To identify tubby related genes involved in retinal degeneration, a human retinal cDNA library was screened with the conserved 3' coding region of human tubby gene as a probe, under low stringency conditions. The TULP1 gene was identified by this screening method. 77% aa identity was observed in the conserved region between TULP1 and TUB. In contrast to TUB, probing a variety of tissue northern blots with TULP1 showed no hybridizing bands. Thus, TULP1 expression is restricted to retina.

Gene specific PCR primers for TULP1 were used to determine its chromosomal location, using the Stanford G3 Radiation Hybrid panel. TULP1 localizes to chromosome 6p21.3. Two markers, D6S439 and D2S291, that flank TULP1 have been reported not to recombine with the RP 14 locus in a human kindred (Shugart et al. (1995) Am J Hum Genet. 57:499–502) demonstrating that TULP1 is tightly linked to the RP 14 locus.

Northern blot analysis of adult human tissues showed that TUB hybridized to a ~7–7.5 kb transcript with strong expression in head, brain, testis, ovary, thyroid, and spinal cord after 48 hour exposure. It was also detected in skeletal muscle, prostate, small intestine, trachea and adrenal gland. A 2.4 kb TUB transcript was observed in liver and thyroid. No bands were observed on the same northern blots when hybridized with a TULP1 probe.

Methods

Adult brain cDNA isolation. To isolate the TUB gene, approximately $1.2 \times 10^6$ plaque forming units of human adult brain cDNA lambda gt11 library were plated according to the manufacturer's instructions (Clontech). $^{32}$P labeled hybridization probes were prepared from two TUB sequences, ET-3636. p01.a04 (nt 1422 to 1593, 171 bp, GenBank Accession No. U52433) and ET-3636.p01.d01 (nt 1323 to 1421, 99 bp) by random hexamer priming, as described previously (Sambrook et al. Molecular Cloning: a Laboratory Manual 2nd ed. (Cold Spring Harbor Laboratory Press, Cold Spring Harbor, 1989)).

Filters lifted from the phage plates were hybridized with labeled probe in 10% dextran sulfate, 1% SDS, 1M NaCl, 100 μg/ml of salmon testes DNA, at 65OC. for 18 hr. After hybridization, filters were washed at 65° C. in 2×SSC, 0.1% SDS for 45 min; 0.2×SSC, 0.1% SDS for 45 min and 0.2×SSC, 0.1% SDS for 45 min. Following plaque purification, cDNA inserts were PCR amplified using lambda gt 11 primers (BRL) and directly cloned into pCR2.1 for sequencing, according to the manufacturer's instructions (Invitrogen). Automated fluorescence sequencing was utilized (Prism, Applied Biosystems).

Retinal cDNA isolation. To identify TULP1, approximately $1 \times 10^6$ pfus of human retinal cDNA lambda gt11 library (Clontech) were hybridized as described above with a $^{32}$P labeled-EcoRI/Sac II fragment (1–962 bp) of Image EST clone 221670 (Research Genetics, Genbank accession no. H92408) at 65° C. overnight. The membranes were washed sequentially for 1 hour each with 2×SSC, 0.1% SDS at 50° C., 1×SSC, 0.1% SDS at 50° C., and 0.5×SSC, 0.1% SDS at 60° C. Positive plaques were purified and processed as above.

Full length cDNA. To isolate the flanking 5' sequences, the Marathon-Ready cDNA kit (Clonetech) was used according to manufacturer's protocol. Amplifications products were gel purified (Qiagen) and sequenced automatically (Prism, Applied Biosystems) or manually by dideoxy cycle sequencing (Sequitherm, Epicentre Technologies). Alternately, gel purified products were subcloned into TA cloning vector according to manufacturer's instruction (BRL), electroporated into DH10B cells, grown, and plasmids isolated by standard protocol prior to sequencing (Ausubel, et al. *Current Protocols in Molecular Biology*. Greene Publishing Associates and Wiley-Interscience, New York, updated to 1995).

Southern analysis. Genomic DNAs from a number of animal species were digested with EcoR I and the DNA transferred to nylon membranes by standard protocol (Clontech). The membranes were hybridized with $^{32}$P labeled Hind III fragment (281–1833 bp) of TUB cDNA, and $^{32}$P labeled-EcoRI/BstX I fragment containing the 5' 365 bp of Image EST clone 221670, which contains the 3' end of TULP1. Blots were washed in 2×SSC, 0.05% SDS at room temp. for 2×10 min. and at 60° C. for 20 min, then twice with 0.2×SSC, 0.1% SDS at 60° C for 20 min. each.

Northern analysis. Human multiple tissue northern blots MTN I, II and III (Clontech) were hybridized with the $^{32}$P labeled Hind III fragment (281–1833 bp) of TUB cDNA and $^{32}$P labeled-EcoRI/BstX I fragment of Image EST clone 221670 in 5× SSPE, 10× Denhardt's, 2%SDS, 100 µg/ml of sheared salmon sperm DNA and 50% formamide at 42° C. for 18 hr, then washed at 2×SSC, 0.05% SDS at room temperature for 3×10 min, and at 0.1×SSC, 0.1% SDS at 50° C. for 2×20 min.

Radiation hybrid mapping. Oligonucleotide primers for PCR amplification were constructed from the novel 5' end of TUB, generating a product of 225 bp for cDNA and ~850 bp for genomic DNA:
(SEQ ID NO:3) CTTAAACCCACTCCATCCTGTG
(SEQ ID NO:4) ATCTCCCTTCCTTCCTTCCAGT.
Amplification primers for the 3' non-coding region for TUB, generating a product of 221 bp were constructed:
(SEQ ID NO:5) TGCCTGGGAATCCTGCTGC;
(SEQ ID NO:6) TCCTAAGGGTCCTGCCACT.
For TULP1, generating a product of 92 bp, the following primers were constructed:
(SEQ ID NO:7) CGAAAACGGAGCAAGACAG;
(SEQ ID NO:8) TATGAGGCTCTCCAGCGTC.
The MacVector computer program (Oxford) was used to design primer sets. After confirming by sequencing that the appropriate product was amplified, the retention patterns for each oligonucleotide pair were obtained by PCR assay in the Stanford G3 Radiation Hybrid panel (Cox et al. (1990) *Science* 250:245–250). Data entered into an online database was analyzed by RHMAP software developed by Boehnke et al. (1991) *Am J Hum Genet* 49:1174–1188.

It is evident from the above results that TULP1 is a novel human gene expressed specifically in retinal tissue. The chromosomal location of TULP1 is tightly linked to the locus for retinitis pigmentosa 14.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated nucleic acid molecule encoding the mammalian TULP1 protein which has the amino acid sequence of SEQ ID NO:2.

2. An isolated nucleic acid molecule encoding mammalian TULP1 protein which has the nucleotide sequence of SEQ ID NO:1.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2116 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
AGAATTCAGC GGCCGCTGAA TTCTAGCAAA GGCACCATGC CTCTGCGGGA TGAAACCCTC      60

CGAGAGGTGT GGGCCTCTGA CAGTGGGCAT GAAGAAGAAA GCCTGAGCCC GGAGGCCCCG     120

CGGCGCCCCA AACAGCGACC CGCCCCGGCA CAGAGGCTAA GGAAGAAGAG GACGGAGGCC     180

CCCGAATCCC CCTGCCCCAC GGGATCCAAG CCCCGGAAGC CCGGAGCTGG GCGGAGGGGG     240

AGGCCGCGGG AGGAGCCTTC CCCAGACCCA GCCCAGGCCC GGGCGCCGCA GACGGTCTAC     300

GCCAGGTTCC TCAGGGACCC CGAGGCCAAG AAGCGCGACC CCCGGGAAAC CTTTCTGGTA     360

GCCCGTGCCC CAGACGCGGA GGACGAGGAG GAGGAGGAAG AGGAGGACGA GGAGGACGAG     420

GAAGAGGAGG CAGAGGAAAA GAAAGAGAAA ATCCTTCTGC CTCCCAAGAA GCCCCTGAGA     480

GAGAAGAGCT CCGCAGACCT GAAGGAGAGG AGGGCCAAGG CCCAGGGCCC AAGGGGAGAC     540
```

-continued

| | | | | | |
|---|---|---|---|---|---|
| CTGGGAAGCC | CTGACCCCCC | ACCGAAACCT | CTGCGTGTTA | GGAATAAGGA | AGCTCCAGCA | 600 |
| GGGGAGGGGA | CCAAGATGAG | AAAGACCAAG | AAGAAAGGGT | CTGGGGAGGC | CGACAAGGAC | 660 |
| CCCTCAGGGA | GCCCAGCCAG | TGCGAGGAAG | AGCCCAGCAG | CCATGTTTCT | GGTTGGGGAA | 720 |
| GRCAGTCCTG | ACAAGAAAGC | CCTGAAGAAG | AAAGGCACTC | CCAAAGGCGC | GAGGAAGGAG | 780 |
| GAAGAAGAGG | AGGAGGAGGC | AGCTACGGTG | ATAAAGAACA | GCAATCAAAA | GGGCAAAGCC | 840 |
| AAAGGAAAAG | GCAAAAAGAA | AGCGAAGGAG | GAGAGGGCCC | CGTCTCCCCC | CGTGGAGGTG | 900 |
| GACGAACCCC | GGGAGTTTGT | GCTCCGGCCT | GCCCCCCAGG | GCCGCACGGT | GCGCTGCCGG | 960 |
| CTGACCCGGG | ACAAAAAGGG | CATGGATCGA | GGCATGTATC | CCTCCTACTT | CCTGCACCTG | 1020 |
| GACACGGAGA | AGAAGGTGTT | CCTCTTGGCT | GGCAGGAAAC | GAAAACGGAG | CAAGACAGCC | 1080 |
| AATTACCTCA | TCTCCATCGA | CCCTACCAAT | CTGTCCCGAG | GAGGGGAGAA | TTTCATCGGG | 1140 |
| AAGCTGAGGT | CCAACCTCCT | GGGGAACCGC | TTCACGGTCT | TTGACAACGG | GCAGAACCCA | 1200 |
| CAGCGTGGGT | ACAGCACTAA | TGTGGCAAGC | CTTCGGCAGG | AGCTGGCAGC | TGTGATCTAT | 1260 |
| GAAACCAACG | TGCTGGGCTT | CCGTGGCCCC | CGGCGCATGA | CCGTCATCAT | TCCTGGCATG | 1320 |
| AGTGCGGAGA | ACGAGAGGGT | CCCCATCCGG | CCCCGAAATG | CTAGTGACGG | CCTGCTGGTG | 1380 |
| CGCTGGCAGA | ACAAGACGCT | GGAGAGCCTC | ATAGAACTGC | ACAACAAGCC | ACCTGTCTGG | 1440 |
| AACGATGACA | GTGGCTCCTA | CACCCTCAAC | TTCCAAGGCC | GGGTCACCCA | GGCCTCAGTC | 1500 |
| AAGAACTTCC | AGATTGTCCA | CGCTGATGAC | CCCGACTATA | TCGTGCTGCA | GTTCGGCCGC | 1560 |
| GTGGCGGAGG | ACGCCTTCAC | CCTAGACTAC | CGGTACCCGC | TGTGCGCCCT | GCAGGCCTTC | 1620 |
| GCCATCGCCC | TCTCCAGTTT | CGACGGGAAG | CTGGCTTGCG | AGTGACCCCA | GCAGCCCTC | 1680 |
| AGCGCCCCCA | GAGCCCGTCA | GCGTGGGGGA | AAGGATTCAG | TGGAGGCTGG | CAGGGTCCCT | 1740 |
| CCAGCAAAGC | TCCCGCGGAA | AACTGCTCCT | GTGTCGGGGC | TGACCTCTCA | CTGCCTCTCG | 1800 |
| GTGACCTCCG | TCCTCTCCCC | AGCCTGGCAC | AGGCCGAGGC | AGGAGGAGCC | CGGACGGCGG | 1860 |
| GTAGGACGGA | GATGAAGAAC | ATCTGGAGTT | GGAGCCGCAC | ATCTGGTTTC | GGAGTTCGCC | 1920 |
| TGCGCCGCTG | TGCCCCCCTC | CTCCCCGCGC | CCCAGTCAAT | TCCTGTCCGG | GAGCAGTAGT | 1980 |
| CATTGTTGTT | TTAACCTCCC | CTCTCCCCGG | GACCGCGCTA | GGGCTCCGAG | GAGCTGGGGC | 2040 |
| GGGCTAGGAG | GAGGGGGTAG | GTGATGGGGG | ACGAGGGCCA | GGCACCCACA | TCCCCAATAA | 2100 |
| AGCCGCGTCC | TTGGCA | | | | | 2116 |

( 2 ) INFORMATION FOR SEQ ID NO:2:

( i ) SEQUENCE CHARACTERISTICS:
        ( A ) LENGTH: 542 amino acids
        ( B ) TYPE: amino acid
        ( C ) STRANDEDNESS: double
        ( D ) TOPOLOGY: linear ( i i ) MOLECULE TYPE: protein ( x i ) SEQUENCE DESCRIPTION: SEQ ID NO:2:

| Met | Pro | Leu | Arg | Asp | Glu | Thr | Leu | Arg | Glu | Val | Trp | Ala | Ser | Asp | Ser |
|---|---|---|---|---|---|---|---|---|---|---|---|---|---|---|---|
| 1 | | | | 5 | | | | | 10 | | | | | 15 | |

| Gly | His | Glu | Glu | Glu | Ser | Leu | Ser | Pro | Glu | Ala | Pro | Arg | Arg | Pro | Lys |
|---|---|---|---|---|---|---|---|---|---|---|---|---|---|---|---|
| | | | 20 | | | | | 25 | | | | | 30 | | |

| Gln | Arg | Pro | Ala | Pro | Ala | Gln | Arg | Leu | Arg | Lys | Lys | Arg | Thr | Glu | Ala |
|---|---|---|---|---|---|---|---|---|---|---|---|---|---|---|---|
| | | 35 | | | | | 40 | | | | | 45 | | | |

| Pro | Glu | Ser | Pro | Cys | Pro | Thr | Gly | Ser | Lys | Pro | Arg | Lys | Pro | Gly | Ala |
|---|---|---|---|---|---|---|---|---|---|---|---|---|---|---|---|
| | 50 | | | | | 55 | | | | | 60 | | | | |

```
Gly Arg Arg Gly Arg Pro Arg Glu Glu Pro Ser Pro Asp Pro Ala Gln
 65                  70                  75                  80

Ala Arg Ala Pro Gln Thr Val Tyr Ala Arg Phe Leu Arg Asp Pro Glu
             85                  90                  95

Ala Lys Lys Arg Asp Pro Arg Glu Thr Phe Leu Val Ala Arg Ala Pro
            100                 105                 110

Asp Ala Glu Asp Glu Glu Glu Glu Glu Glu Asp Glu Glu Asp Glu
        115                 120                 125

Glu Glu Glu Ala Glu Glu Lys Lys Glu Lys Ile Leu Leu Pro Pro Lys
        130                 135                 140

Lys Pro Leu Arg Glu Lys Ser Ser Ala Asp Leu Lys Glu Arg Arg Ala
145                 150                 155                 160

Lys Ala Gln Gly Pro Arg Gly Asp Leu Gly Ser Pro Asp Pro Pro Pro
                165                 170                 175

Lys Pro Leu Arg Val Arg Asn Lys Glu Ala Pro Ala Gly Glu Gly Thr
            180                 185                 190

Lys Met Arg Lys Thr Lys Lys Lys Gly Ser Gly Glu Ala Asp Lys Asp
        195                 200                 205

Pro Ser Gly Ser Pro Ala Ser Ala Arg Lys Ser Pro Ala Ala Met Phe
        210                 215                 220

Leu Val Gly Glu Xaa Ser Pro Asp Lys Lys Ala Leu Lys Lys Lys Gly
225                 230                 235                 240

Thr Pro Lys Gly Ala Arg Lys Glu Glu Glu Glu Glu Glu Glu Ala Ala
            245                 250                 255

Thr Val Ile Lys Asn Ser Asn Gln Lys Gly Lys Ala Lys Gly Lys Gly
            260                 265                 270

Lys Lys Lys Ala Lys Glu Glu Arg Ala Pro Ser Pro Pro Val Glu Val
        275                 280                 285

Asp Glu Pro Arg Glu Phe Val Leu Arg Pro Ala Pro Gln Gly Arg Thr
        290                 295                 300

Val Arg Cys Arg Leu Thr Arg Asp Lys Lys Gly Met Asp Arg Gly Met
305                 310                 315                 320

Tyr Pro Ser Tyr Phe Leu His Leu Asp Thr Glu Lys Lys Val Phe Leu
            325                 330                 335

Leu Ala Gly Arg Lys Arg Lys Arg Ser Lys Thr Ala Asn Tyr Leu Ile
            340                 345                 350

Ser Ile Asp Pro Thr Asn Leu Ser Arg Gly Gly Glu Asn Phe Ile Gly
        355                 360                 365

Lys Leu Arg Ser Asn Leu Leu Gly Asn Arg Phe Thr Val Phe Asp Asn
370                 375                 380

Gly Gln Asn Pro Gln Arg Gly Tyr Ser Thr Asn Val Ala Ser Leu Arg
385                 390                 395                 400

Gln Glu Leu Ala Ala Val Ile Tyr Glu Thr Asn Val Leu Gly Phe Arg
            405                 410                 415

Gly Pro Arg Arg Met Thr Val Ile Ile Pro Gly Met Ser Ala Glu Asn
            420                 425                 430

Glu Arg Val Pro Ile Arg Pro Arg Asn Ala Ser Asp Gly Leu Leu Val
        435                 440                 445

Arg Trp Gln Asn Lys Thr Leu Glu Ser Leu Ile Glu Leu His Asn Lys
450                 455                 460

Pro Pro Val Trp Asn Asp Asp Ser Gly Ser Tyr Thr Leu Asn Phe Gln
465                 470                 475                 480

Gly Arg Val Thr Gln Ala Ser Val Lys Asn Phe Gln Ile Val His Ala
            485                 490                 495
```

|  |  |  |  |  |  |  |  |  |  |  |  |  |  |  |
|---|---|---|---|---|---|---|---|---|---|---|---|---|---|---|
| Asp | Asp | Pro | Asp<br>500 | Tyr | Ile | Val | Leu | Gln<br>505 | Phe | Gly | Arg | Val<br>510 | Ala | Glu | Asp |
| Ala | Phe | Thr<br>515 | Leu | Asp | Tyr | Arg | Tyr<br>520 | Pro | Leu | Cys | Ala<br>525 | Leu | Gln | Ala | Phe |
| Ala | Ile | Ala<br>530 | Leu | Ser | Ser | Phe<br>535 | Asp | Gly | Lys | Leu | Ala<br>540 | Cys | Glu |

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="primers"

( x i ) SEQUENCE DESCRIPTION: SEQ ID NO:3:

CTTAAACCCA CTCCATCCTG TG                22

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="primers"

( x i ) SEQUENCE DESCRIPTION: SEQ ID NO:4:

ATCTCCCTTC CTTCCTTCCA GT                22

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="primers"

( x i ) SEQUENCE DESCRIPTION: SEQ ID NO:5:

TGCCTGGGAA TCCTGCTGC                  19

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="primers"

( x i ) SEQUENCE DESCRIPTION: SEQ ID NO:6:

TCCTAAGGGT CCTGCCACT                  19

( 2 ) INFORMATION FOR SEQ ID NO:7:

( i ) SEQUENCE CHARACTERISTICS:
        ( A ) LENGTH: 19 base pairs
        ( B ) TYPE: nucleic acid ( C ) STRANDEDNESS: single
        ( D ) TOPOLOGY: linear ( i i ) MOLECULE TYPE: other nucleic acid
        ( A ) DESCRIPTION: /desc ="primers"

( x i ) SEQUENCE DESCRIPTION: SEQ ID NO:7:

CGAAAACGGA GCAAGACAG 19

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="primers"

( x i ) SEQUENCE DESCRIPTION: SEQ ID NO:8:

TATGAGGCTC TCCAGCGTC 19